(12) United States Patent
Vaughan et al.

(10) Patent No.: US 12,178,778 B2
(45) Date of Patent: Dec. 31, 2024

(54) SMART CONTAINER

(71) Applicant: Evernorth Strategic Development, Inc., St. Louis, MO (US)

(72) Inventors: Moses Vaughan, Nutley, NJ (US); Christopher M. Myers, Dublin, OH (US); Bill Loi Pham, Highlands Ranch, CO (US)

(73) Assignee: Evernorth Strategic Development, Inc., St. Louis, MO (US)

( * ) Notice: Subject to any disclaimer, the term of this patent is extended or adjusted under 35 U.S.C. 154(b) by 447 days.

(21) Appl. No.: 17/554,068

(22) Filed: Dec. 17, 2021

(65) Prior Publication Data

US 2023/0190579 A1    Jun. 22, 2023

(51) Int. Cl.
*A61J 1/03* (2023.01)
*A61J 7/00* (2006.01)
(Continued)

(52) U.S. Cl.
CPC ............... *A61J 1/03* (2013.01); *A61J 7/0076* (2013.01); *G16H 20/13* (2018.01); *A61J 7/02* (2013.01);
(Continued)

(58) Field of Classification Search
CPC ........ G01G 23/361; Y10S 177/06; A61J 1/03; A61J 2200/74; A61J 2200/70; G01N 2021/1742
(Continued)

(56) References Cited

U.S. PATENT DOCUMENTS 4,536,651 A * 8/1985 Bosse ................... G01L 1/241
    359/833
6,016,703 A * 1/2000 Blyler, Jr. ............. G01L 1/24
    250/231.19

(Continued)

FOREIGN PATENT DOCUMENTS

CN    105009046 A * 10/2015 ........... G06F 3/0421
CN    105125411 A * 12/2015
(Continued)

OTHER PUBLICATIONS

AAFP, Peer Support Networks Can Be a Healthy Supplement to Physician Practices, 6. https://www.aafp.org/news/health-of-the-public/20140319peersupportwebinar.html, Mar. 19, 2014.
(Continued)

*Primary Examiner* — Mollie Impink
(74) *Attorney, Agent, or Firm* — Jordan IP Law, LLC

(57) ABSTRACT

A system for monitoring access to a contained medication is disclosed. The system includes a server configured to store user information for each of a plurality of registered users. The system also includes a smart container configured to hold a medication. The smart container includes a processor configured to (a) detect a user device of a user in possession of the smart container, (b) determine if the user device is associated with one of the registered users, and (c) if the determination is affirmative, manage a user session with the user device and transmit one or more session messages to the server. The server is configured to store a transaction corresponding to each of the session messages to thereby create a transaction history for the smart container.

23 Claims, 12 Drawing Sheets

(51) Int. Cl.
*A61J 7/02* (2006.01)
*G16H 20/13* (2018.01)

(52) U.S. Cl.
CPC ........ *A61J 2200/70* (2013.01); *A61J 2200/74* (2013.01)

(58) Field of Classification Search
USPC .................................................. 177/DIG. 6
See application file for complete search history.

(56) References Cited

U.S. PATENT DOCUMENTS

| | | | | |
|---|---|---|---|---|
| 6,872,895 | B2* | 3/2005 | Cochran | G01G 15/00 177/1 |
| 8,984,170 | B2 | 3/2015 | Colrain | |
| 9,225,754 | B2 | 12/2015 | Boysen | |
| 9,485,634 | B2 | 11/2016 | Krishnarao | |
| 9,832,183 | B2 | 11/2017 | Ganesan | |
| 9,860,245 | B2 | 1/2018 | Ronda | |
| 9,912,488 | B2 | 3/2018 | Chastain | |
| 9,947,061 | B2 | 4/2018 | Sexton | |
| 10,694,032 | B2 | 6/2020 | Byrne | |
| 2007/0125937 | A1* | 6/2007 | Eliasson | G06F 3/0421 250/221 |
| 2014/0048593 | A1 | 2/2014 | Hoganson | |
| 2014/0092052 | A1* | 4/2014 | Grunthaner | G06F 3/044 345/173 |
| 2014/0279647 | A1 | 9/2014 | Tolcher | |
| 2015/0026062 | A1 | 1/2015 | Paulsen | |
| 2015/0272825 | A1* | 10/2015 | Lim | G16H 40/67 340/5.2 |
| 2016/0022541 | A1 | 1/2016 | Dalal | |
| 2016/0030673 | A1* | 2/2016 | White | G16H 10/60 702/50 |
| 2016/0048657 | A1* | 2/2016 | LeBrun | A61J 1/1412 705/2 |
| 2016/0361234 | A1* | 12/2016 | Li | A61J 7/049 |
| 2017/0076065 | A1 | 3/2017 | Darr | |
| 2017/0132393 | A1 | 5/2017 | Natarajan | |
| 2018/0172799 | A1 | 6/2018 | Meadow | |
| 2021/0151159 | A1 | 5/2021 | Childress | |
| 2022/0339071 | A1* | 10/2022 | Gilreath | A61J 7/0076 |

FOREIGN PATENT DOCUMENTS

| | | | | |
|---|---|---|---|---|
| CN | 114365231 | A * | 4/2022 | G06F 21/32 |
| DE | 10039094 | C1 * | 2/2002 | G01D 5/26 |

OTHER PUBLICATIONS

Bayer, http://pharma.bayer.com/en/commitment-responsibility/benefits-and-risks-of-drugs/medication-adherence/, accessed as early as Nov. 15, 2019.

Brown, The Psychology of Gamification: Why It Works (& How To Do It!), https://www.bitcatcha.com/blog/gamify-website-increase-engagement/, accessed as early as Nov. 15, 2019.

Healthprize, Medication Adherence: Pharma's $637 Billion Opportunity, 2. https://healthprize.com/blog/medication-adherence-pharmas-637-billion-opportunity/, accessed as early as Nov. 15, 2019.

Kim, Medication Adherence: The Elephant in the Room, https://www.uspharmacist.com/article/medication-adherence-the-elephant-in-the-room#targetText=ABSTRACT%3A%20Medication%20adherence%20can%20have,chronic%20medications%20is%20about%2050%25.&targetText=Adherence%20rates%20can%20go%20down,as%20barriers%20emerge%20or%20multiply. Jan. 19, 2018.

Nansel, Diabetes Personal Trainer Outcomes, Diabetes Care, vol. 30, No. 10, Oct. 2007, https://care.diabetesjournals.org/content/30/10/2471.short.

Nuemd, 4 Ways to Address Medication Adherence, http://pharma.bayer.com/en/commitment-responsibility/benefits-and-risks-of-drugs/medication-adherence/, accessed as early as Nov. 15, 2019.

Pillsy Digest, 15 Frightening Stats on Medication Adherence (Plus Infographic), 2. https://healthprize.com/blog/medication-adherence-pharmas-637-billion-opportunity/, May 16, 2018.

* cited by examiner

SMART CONTAINER

CROSS-REFERENCE TO RELATED APPLICATIONS

Not applicable.

STATEMENT REGARDING FEDERALLY SPONSORED RESEARCH OR DEVELOPMENT

Not applicable.

STATEMENT REGARDING JOINT RESEARCH AGREEMENT

Not applicable.

BACKGROUND OF THE INVENTION

Pharmaceutical fulfillment systems fill a large number of prescription orders with a variety of medications. Generally, a pharmacist fills each prescription order by placing a specific quantity of medication (e.g., 30, 60, 90 pills) in a container. A logistics company then transports the container to the consumer who placed the prescription order. The consumer then opens the container and consumes the medication as prescribed. In some cases, a family member or caretaker receives the container and administers the medication to the consumer. Thus, several individuals may handle the container along the pharmaceutical distribution supply chain.

A number of different events may occur that prevent the consumer from consuming the medication as intended. For example, the container may be lost, stolen or tampered with before it reaches the consumer. There may also be problems with the medication itself, such as medication that is recalled, medication that is erroneously provided to the consumer, or medication that is prescribed based on a misdiagnosis of the consumer's underlying health condition. Further, there may be problems with medication adherence, which can be particularly problematic with consumers who are required to manage multiple medications or otherwise fail to take one or more medications as prescribed. While advancements have been made to address some of these problems, there remains a need in the art for a technological solution that offers features, functionality or other advantages not provided by existing systems and methods.

BRIEF SUMMARY OF THE INVENTION

The present invention is directed to systems and methods for monitoring access to medications that are provided to consumers within smart containers. In general, all users who have a role in handling one or more smart containers are able to register with a central server. The central server stores user information for each registered user, such as a user identifier and/or a role designation that identifies a role of the registered user in the chain of custody of one or more smart containers (e.g., allowed to transport, allowed to open, etc.). Each registered user has a user device that stores user identifier and/or role designation of the user. The user device may comprise, for example, a smartphone, a personal computing tablet, a smart watch, a wearable device, a key fob, a medical identification bracelet, or any other electronic device capable of storing information and communicating with a smart container and/or the central server.

In some embodiments, the smart container is configured to detect the user device of each user in possession of the smart container. Upon detection of the user device, the smart container determines whether the user device is associated with one of the registered users. If the determination is affirmative, the smart container manages a user session with the user device and transmits one or more session messages to the server. The session messages may be associated with the user identifier of the registered user and/or a container identifier stored on the smart container. The server then stores a transaction corresponding to each of the session messages to thereby create a historical ledger for the smart container. This process is performed for each registered user who handles the smart container during its life cycle. Of course, if the smart container detects a user device that is not associated with one of the registered users, the smart container may transmit a notification to the server for further assessment and possible locking of the smart container and/or return of the smart container to the sender.

In some embodiments, the smart container detects one or more events or "state transitions" that occur during a user session, such as movement of the smart container, opening of the smart container, extraction of contents from the smart container, or addition of contents to the smart container. The smart container also determines whether each state transition is a permitted activity for the registered user based on the user's role designation. For example, a registered user having a "consumer" role designation would be allowed to open the smart container, but a registered user having a "transporter" role designation would typically not have opening rights. Thus, the smart container is able to detect improper handling of the smart container and transmit a notification to the server for further assessment and possible locking of the smart container and/or return of the smart container to the sender.

In some embodiments, the server provides notifications to the smart container and/or the user device of the consumer. These notifications may comprise an adherence status, refill reminders, availability updates, content warnings, chain of custody updates, and the like. Further, in some embodiments, the smart container provides dispensation instructions via an output device, such as an electronic display or one or more light emitting diodes (LEDs) provided on the container. If the smart container is part of a group of smart containers (e.g., if the consumer takes multiple medications), the server is configured to manage each of the smart containers so that the appropriate dispensation instructions are provided to each smart container within the group.

Various embodiments of the present invention are described in detail below, or will be apparent to one skilled in the art based on the disclosure provided herein, or may be learned from the practice of the invention. It should be understood that the above brief summary of the invention is not intended to identify key features or essential components of the embodiments of the present invention, nor is it intended to be used as an aid in determining the scope of the claimed subject matter as set forth below.

BRIEF DESCRIPTION OF THE DRAWINGS

A detailed description of various exemplary embodiments of the present invention is provided below with reference to the following drawings, in which.

DETAILED DESCRIPTION OF EXEMPLARY EMBODIMENTS

Figure 1:
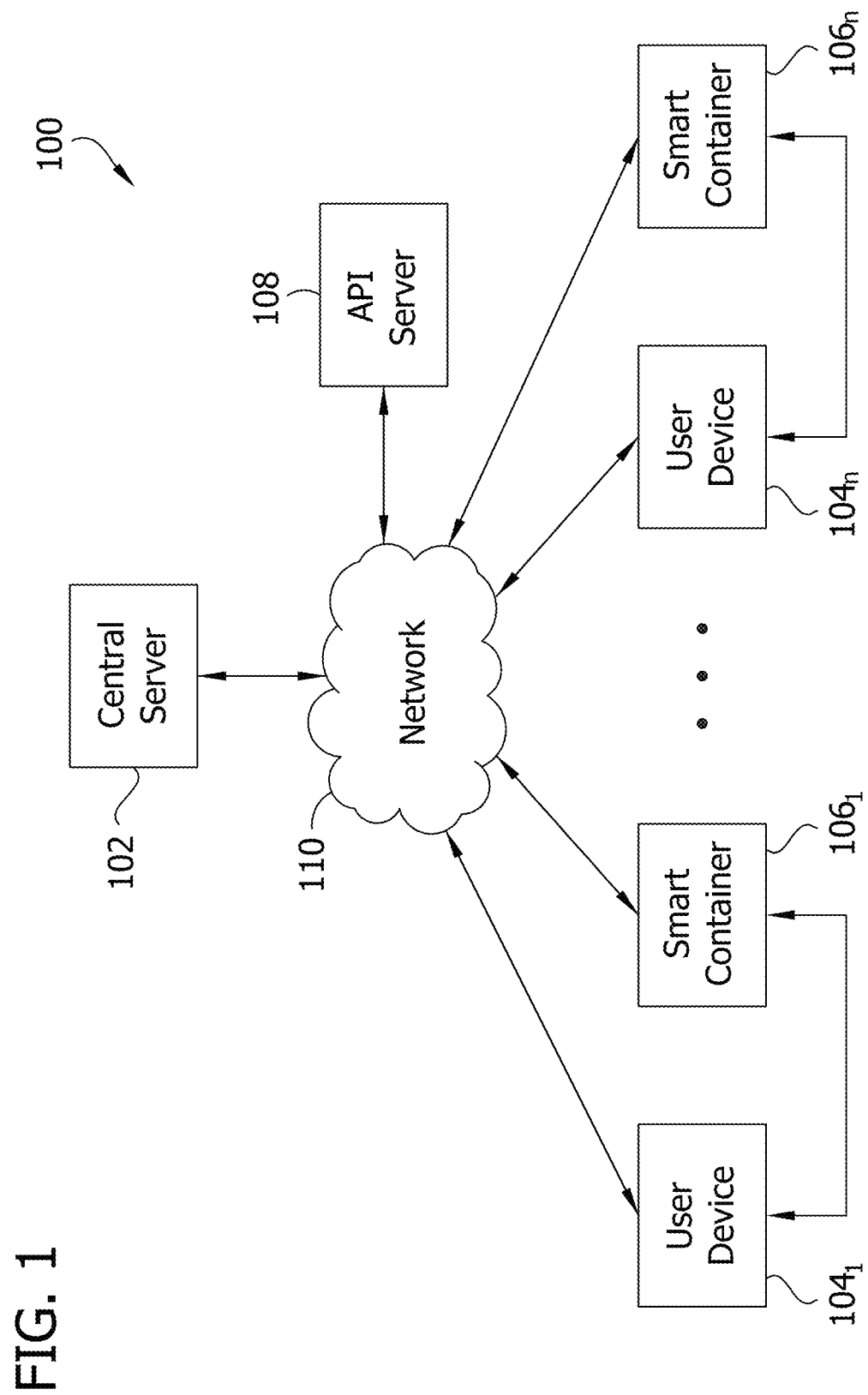
FIG. 1 is a network diagram of a system for providing a smart container platform in accordance with one embodiment of the invention.

The present disclosure is directed to systems and methods for monitoring access to medications provided within smart containers. While the invention will be described in detail below with reference to various exemplary embodiments, it should be understood that the invention is not limited to the specific configurations or methods of any of these embodiments. In addition, although the exemplary embodiments are described as embodying several different inventive features, those skilled in the art will appreciate that any one of these features could be implemented without the others in accordance with the invention.

In the present disclosure, references to "one embodiment," "an embodiment," "an exemplary embodiment," or "embodiments" mean that the feature or features being described are included in at least one embodiment of the invention. Separate references to "one embodiment," "an embodiment," "an exemplary embodiment," or "embodiments" in this disclosure do not necessarily refer to the same embodiment and are also not mutually exclusive unless so stated and/or except as will be readily apparent to one skilled in the art from the description. For example, a feature, structure, function, etc. described in one embodiment may also be included in other embodiments, but is not necessarily included. Thus, the present invention can include a variety of combinations and/or integrations of the embodiments described herein.

A smart container platform is described below in which a central server enables all individuals who have a need to access one or more smart containers to register with the platform. As used herein, the term "access" is intended to mean any activity in which an individual handles or otherwise interacts with a smart container, such as, but not limited to, moving a smart container, opening a smart container, adding and/or removing contents from a smart container, or transporting a smart container. The registration process enables each individual to obtain a unique identifier and a role designation within the smart container platform. The role designation may comprise a role that defines one or more activities permitted to be performed by an individual or simply a list of permitted activities, examples of which are shown in Table 1 below:

TABLE 1

| Role | Permitted Activities | Example(s) |
| --- | --- | --- |
| manipulator | open a smart container; add contents to and/or remove contents from a smart container [note: a container agnostic role that can be applied to multiple smart containers] | pharmacist or medical professional |
| transporter | transport a smart container between physical locations [note: a container agnostic role that can be applied to multiple smart containers] | employee of a logistics company |
| receiver | move a smart container [note: a container specific role that applies to a specific smart container] | family member or caretaker |
| consumer | move a smart container; open a smart container; remove contents from a smart container [note: a container specific role that applies to a specific smart container] | patient |

Of course, it should be understood that the available role designations are not limited to the roles and/or permitted activities shown in Table 1 above and that other role designations may be used within the scope of the present invention.

Each smart container is associated with an acknowledged set of individuals who are authorized to access that smart container. For example, when a patient orders a prescription for fulfillment, a pharmacist who is tasked with filling the prescription will initialize a smart container with the central server. The smart container may be an available smart container in the possession of the pharmaceutical fulfillment system or a smart container provided by the patient. Upon initialization, the smart container will notify its presence to the central server, such as by transmitting a unique container identifier to the central server. The pharmacist then fills the prescription by opening the smart container, adding the prescribed medication, and closing the smart container. The pharmacist may also use a software application or online interface to register the medication information and dosage instructions for the smart container with the central server.

Once the smart container has been filled with the appropriate medication, logistics company personnel transport the smart container from the place of fulfillment to a designated location, such as the address of the patient. A family member may handle the intake of the smart container on behalf of the patient, or the smart container may be received directly by the patient. The patient may then open and remove the medication from the smart container. Thus, in this example, the acknowledged set includes the pharmacist, the logistics company personnel, the family member, and the patient.

During the life cycle of the smart container, the central server receives messages relating to various types of access to the smart container by the individuals within the acknowledged set. For example, all transfers of the smart container between individuals within the acknowledged set are logged with the central server. Preferably, other events are also logged with the central server, such as movement of the smart container, opening of the smart container, extraction of contents from the smart container, or addition of contents to the smart container. This enables the creation of a full transaction history of the smart container and ensures that access is only allowed to those individuals within the acknowledged set. Any violations of access are written to the transaction history and may cause locking of the smart container and/or return of the smart container to the sender.

The central server may also communicate various notifications to one or more individuals within the acknowledged set, either via transmission of information to a user device (e.g., a smartphone) of the individual and/or via the display of information on an onboard display of the smart container. Adherence and usage patterns may also be analyzed complete with thresholds being set and associated warnings/alarms being triggered.

System Configurations

Referring to FIG. 1, a system for providing a smart container platform in accordance with one embodiment of the present invention is shown generally as reference number 100. System 100 includes a central server 102 that communicates with a plurality of network elements—i.e., a plurality of user devices $104_1$-$104_n$, a plurality of smart containers $106_1$-$106_n$, and an application programming interface (API) server 108—via a network 110. Central server 102 will be described in greater detail below with reference to FIG. 2, user devices $104_1$-$104_n$ will be described in greater detail below with reference to FIG. 3, and smart containers $106_1$-$106_n$, will be described in greater detail below with reference to FIGS. 4-8.

Network 110 may comprise any network or combination of networks capable of facilitating the exchange of data among the network elements of system 100. In some embodiments, network 110 enables communication in accordance with one or more cellular standards, such as the Long-Term Evolution (LTE) standard, the Universal Mobile Telecommunications System (UMTS) standard, and the like. In other embodiments, network 110 enables communication in accordance with the IEEE 802.3 protocol (e.g., Ethernet) and/or the IEEE 802.11 protocol (e.g., Wi-Fi). Of course, other types of networks may also be used within the scope of the present invention.

Central Server

Figure 2:
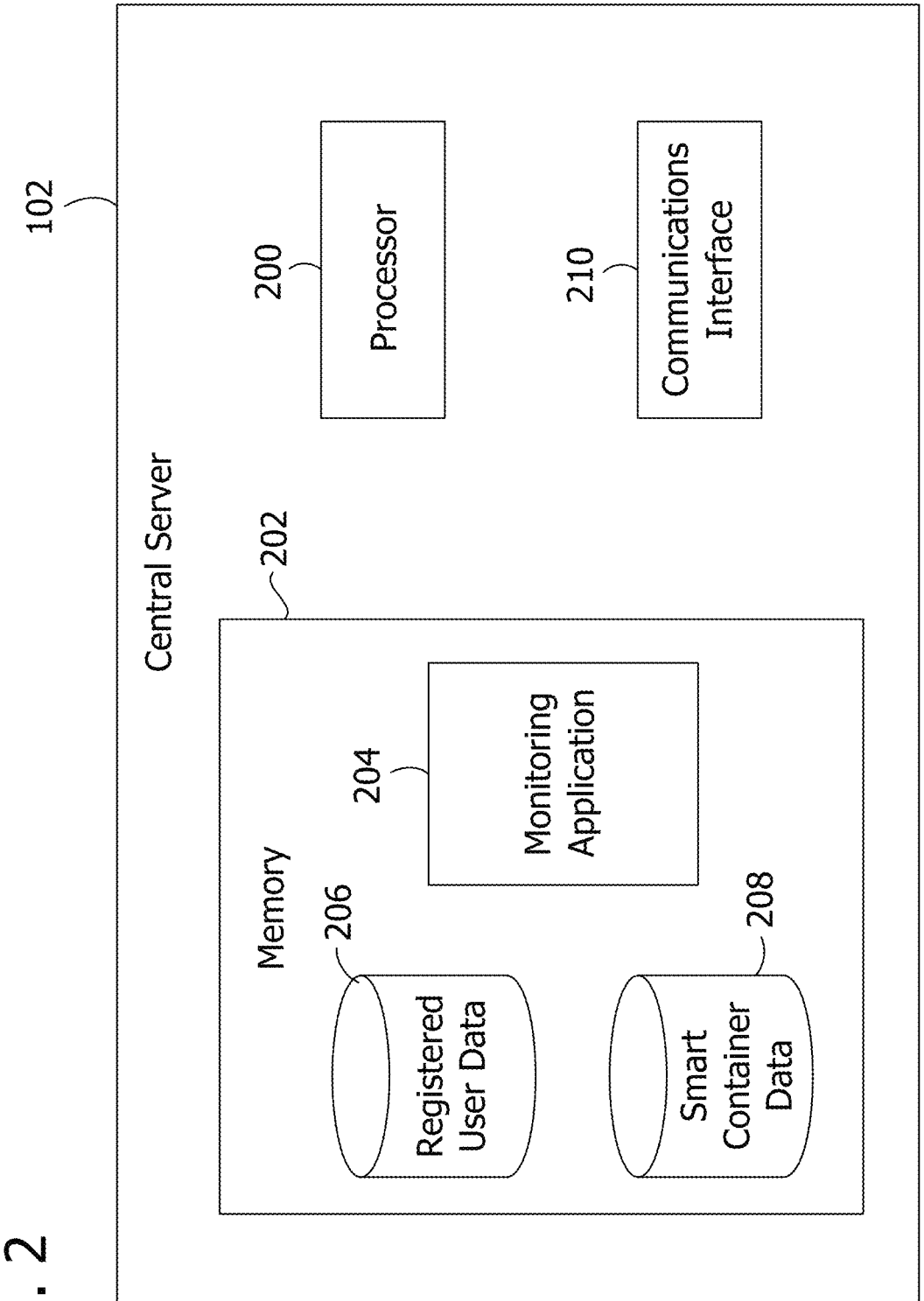
FIG. 2 is a block diagram of the central server shown in FIG. 1.

FIG. 2 is a block diagram illustrating an exemplary embodiment of central server 102 that may be used within system 100. Central server 102 includes a processor 200 that is operatively connected to various hardware and software components, which together enable central server 102 to monitor access to medications provided within smart containers $106_1$-$106_n$ and perform other methods as described herein. Processor 200 may comprise a multi-core processor, multiple processors, or some other type of processor, depending on the particular implementation.

Processor 200 is operatively connected to a memory 202, which may be fixed or removable. Memory 202 may include any suitable combination of volatile memory (e.g., random-access memory (RAM)) and non-volatile memory (e.g. read-only memory (ROM), electrically erasable programmable read-only memory (EEPROM), or flash memory).

Memory 202 stores one or more software programs or applications, such as monitoring application 204, as well as one or more databases, such as a registered user database 206 and a smart container database 208.

Monitoring application 204 includes one or more software modules each of which comprises instructions that, when executed by processor 200, cause processor 200 to perform the methods described herein. In this embodiment, monitoring application 204 includes a registration module that enables users to register with central server 102 (described below with reference to FIG. 9), a transaction module that enables central server 102 to create a transaction history for each of smart containers $106_1$-$106_n$ (described below with reference to FIGS. 11A-111B), and a notification module that transmits notifications and other information to user devices $104_1$-$104_n$ and/or smart containers $106_1$-$106_n$ (described below with reference to FIG. 12).

Registered user database 206 contains user information for each user who is registered to access one or more of smart containers $106_1$-$106_n$. In this embodiment, the user information for each registered user comprises a user profile that includes a user identifier and a role designation within the smart container platform. The user identifier may comprise, for example, a globally unique identifier (GUID) or any other type of unique credentials. The role designation may comprise a role (e.g., manipulator, transporter, receiver, consumer, etc.) that defines one or more activities permitted to be performed by an individual or simply a list of permitted activities (e.g., allowed to transport, allowed to open, etc.). Examples of these roles and permitted activities are shown in Table 1 above. It will be seen that the user identifier and role designation are also stored within the user device of the registered user, as described below.

Smart container database 208 contains data associated with each of smart containers $106_1$-$106_n$. Examples of such data include chain of custody information (e.g., the user identifier and/or role designation of each registered user who accesses the smart container) and/or information on events or "state transitions" that occur during access to a smart container (e.g., movement of the smart container, opening of the smart container, extraction of contents from the smart container, or addition of contents to the smart container). In this embodiment, the data associated with each smart container is stored in association with a container identifier for the smart container and preferably includes a time stamp for each event. It will be seen that the container identifier is also stored within the smart container itself, as described below.

In some embodiments, all or a portion of the data associated with each of smart containers $106_1$-$106_n$ is stored on a distributed ledger for enhanced security, transparency and immutability (i.e., as an alternative to storage of the data in smart container database 208). In these embodiments, processor 200 can make an API call to API server 108 and transmit the data associated with a smart container over network 110 to API server 108. API server 108 then records the data as transactions on a distributed ledger for the smart container. In one embodiment, the distributed ledger comprises a block chain-based distributed ledger, such as any of the enterprise-grade block chain frameworks developed under the Hyperledger project.

Central server 102 further includes a communications interface 210 that is operatively connected to processor 200. Communications interface 210 may be any interface that enables communication between central server 102 and other network elements (including user devices $104_1$-$104_n$, smart containers $106_1$-$106_n$, and API server 108) via network 110. In some embodiments, the communications interface 210 comprises a network interface card (NIC), an integrated network interface, and/or any other interfaces for connecting central server 102 to other network elements and/or communication networks. Such connections can include a wired connection or a wireless connection.

In the embodiment shown in FIG. 1, central server 102 is used to store monitoring application 204, registered user database 206, and smart container database 208, which enable performance of the methods described herein. Of course, other embodiments may include additional servers for performing some of these methods, which may be co-located in the same geographic location or located in different geographic locations and connected to each other via network 110. For example, all or a portion of the various modules of monitoring application 204 could be stored on one or more application servers that may be accessed via network 110. Further, all or a portion of the data contained in registered user database 206 and/or smart container database 208 could be stored on one or more database servers that may be accessed via network 110. Thus, the system may be implemented with any number and combination of servers that are either co-located or geographically dispersed.

User Devices

Referring back to FIG. 1, the individuals who have registered with the smart container platform each carry a user device, i.e., one of user devices $104_1$-$104_n$, which may comprise any electronic device capable of storing information (including the user identifier and/or role designation of the registered user) and communicating with one or more smart containers $106_1$-$106_n$ and/or central server 102. Examples of user devices include a smartphone, a personal computing tablet, a smart watch, a wearable device, a key fob, and a medical identification bracelet. Preferably, each of user devices $104_1$-$104_n$ includes suitable components to enable practice of the invention, such as: a processor; a memory; a power supply; an electronic display and/or one or more light emitting diodes (LEDs); an accelerometer and gyroscope; a short-range wireless transceiver that enables communication with one of smart containers $106_1$-$106_n$; and a long-range wireless transceiver that enables communication with central server 102. Of course, it should be understood that each of user devices $104_1$-$104_n$ may not include all of these components and/or may include additional components that are not listed above.

Figure 3:
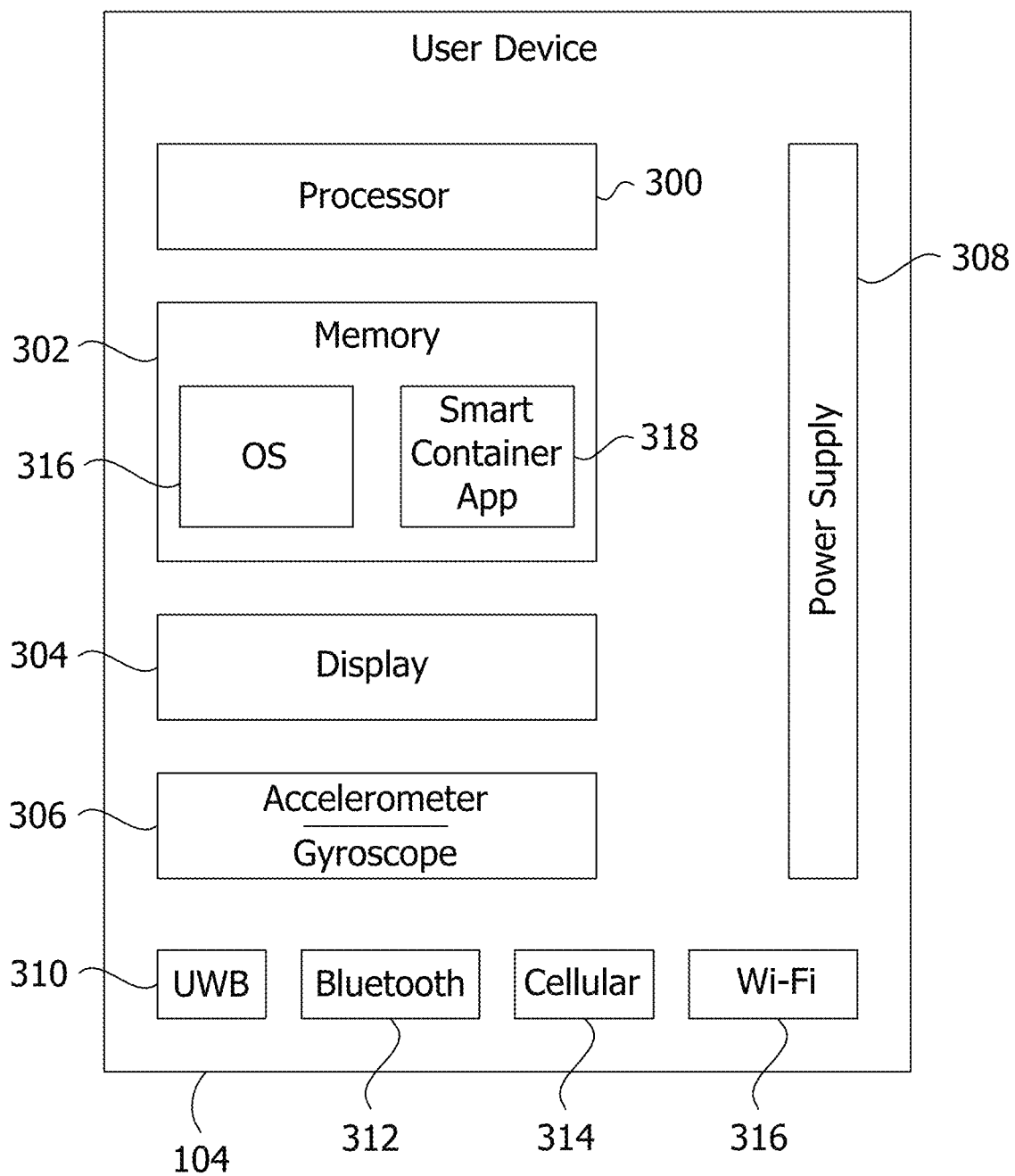
FIG. 3 is a block diagram of an exemplary smartphone that may be used as one of the user devices shown in FIG. 1.

FIG. 3 is a block diagram illustrating an exemplary embodiment of a user device 104 that may be used as one of user devices $104_1$-$104_n$. In this embodiment, user device 104 includes a processor 300 that is operatively connected to various hardware and software components, including a memory 302, a display 304, an accelerometer and gyroscope 306, a power supply 308, and a wireless communications subsystem that includes an ultra-wideband (UWB) transceiver 310, a Bluetooth transceiver 312, a cellular transceiver 314, and a Wi-Fi transceiver 316.

Processor 300 may comprise a central processing unit (CPU), a multi-core processor, multiple processors, or some other type of processor, depending on the particular implementation. Processor 300 is operatively connected to memory 302, which may comprise any suitable combination of volatile memory (e.g., random-access memory (RAM)) and non-volatile memory (e.g. read-only memory (ROM), electrically erasable programmable read-only memory (EEPROM), or flash memory). Memory 302 stores an operating system 316 and a smart container application 318 (along with the user identifier and/or role designation of the registered user).

Smart container application 318 refers generally to an application for user device 104 that facilitates integration of user device 104 within the smart container platform. Smart container application 318 comprises instructions that, when executed by processor 300, cause processor 300 and the various hardware components of user device 104 to perform the methods described herein. Smart container application 318 may be downloaded over network 110 via cellular communication interface 314, either from central server 102 or any other server that provides the application for download to user device 104. It will be seen that smart container application 318 enables an individual using user device 104 to register with central server 102 (at which time user device 104 receives a user identifier and/or role designation), communicate with one or more of smart containers $106_1$-$106_n$ and central server 102 in connection with access to the smart container, and receive notifications and other access-related information from central server 102, as described below.

Processor 300 is also operatively connected to display 304. In this embodiment, display 304 comprises a touch screen display configured to provide a graphical user interface that enables the registered user to complete the registration process, such as by presenting various fields that allow for the entry of registration information. The graphical user interface of display 304 also presents notifications and other access-related information to the registered user. Exemplary displays include, but are not limited to, a liquid crystal display (LCD), an organic light emitting diode (OLED), an active matrix organic light emitting diode (AMOLED), and the like.

Processor 300 is also operatively connected to accelerometer and gyroscope 306, which are configured to detect the orientation and rotation, respectively, of user device 104. Also, power supply 308 is provided to supply power to the components of user device 104. In this embodiment, power supply 308 comprises a rechargeable battery. Of course, other types of power sources may also be used in accordance with the present invention.

Processor 300 is also operatively connected to UWB transceiver 310 and Bluetooth transceiver 312 each of which enables short-range communication with one of smart containers $106_1$-$106_n$. UWB transceiver 310 is configured to enable communication with one of smart containers $106_1$-$106_n$ in accordance with the IEEE 802.15.4 protocol. Bluetooth transceiver 312 is configured to enable communication with one of smart containers $106_1$-$106_n$ in accordance with the IEEE 802.15.1 protocol. Of course, other types of communication interfaces may also be used in accordance with the present invention (e.g., Wi-Fi Direct).

In some cases, the registered user carrying user device 104 accesses a smart container that supports UWB (but not Bluetooth), in which case UWB transceiver 310 is used to communicate with the smart container. In other cases, the registered user carrying user device 104 accesses a smart container that supports Bluetooth (but not UWB), in which case Bluetooth transceiver 312 is used to communicate with the smart container. In yet other cases, the registered user carrying user device 104 accesses a smart container that includes both UWB and Bluetooth capabilities (e.g., smart container 106 described below). In that case, UWB transceiver 310 is preferably used as the default for communication with the smart container due to the superior performance capabilities of UWB compared to other short-range communication protocols, as discussed below.

Processor 300 is also operatively connected to cellular transceiver 314 and Wi-Fi transceiver 316 each of which enables long-range communication with central server 102. Cellular transceiver 314 is configured to enable communication with central server 102 in accordance with a cellular protocol, such as those that operate using the Long-Term Evolution (LTE) standard, the Universal Mobile Telecommunications System (UMTS) standard, and the like. Wi-Fi transceiver 316 is configured to enable communication with a local Wi-Fi network in accordance with the IEEE 802.11 protocol, wherein the local Wi-Fi network enables communication with central server 102. Of course, other types of communication interfaces may also be used in accordance with the present invention.

Smart Containers

Figure 4:
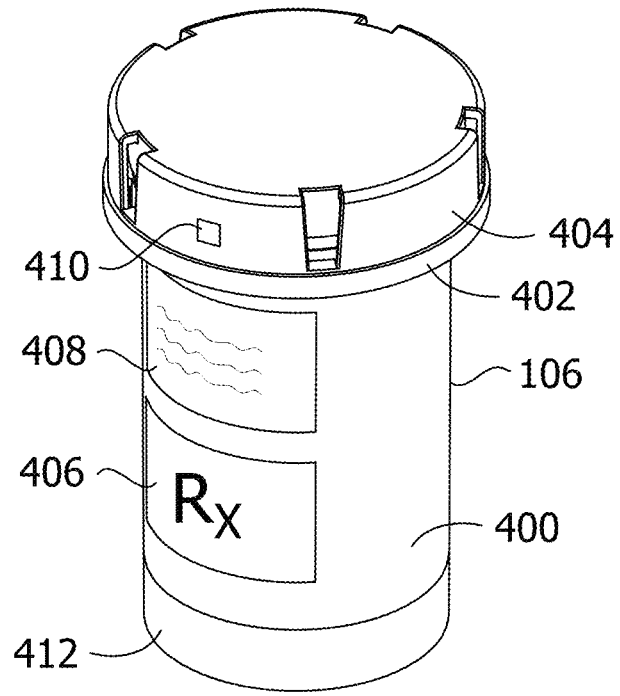
FIG. 4 is a front perspective view of an exemplary smart container that includes an electronic display for providing notifications, which may be used as one of the smart containers shown in FIG. 1.

FIG. 4 illustrates an exemplary embodiment of a smart container 106 that may be used as one of smart containers 106₁-106ₙ. Smart container 106 includes a container body 400 that defines an interior cavity for holding a specific quantity of medication (e.g., 30, 60, 90 pills). Container body 400 includes a lip 402 that defines an opening at its top end that is closeable with a cap 404 to retain the medication therein. In this embodiment, container body 400 has a circular cross-section and is made of materials similar to those used for conventional prescription bottles (e.g., polypropylene (plastic #5) or other recyclable plastics), although containers having a variety of shapes and sizes and made of different materials may be used in accordance with the present invention.

Affixed to container body 400 is a prescription label 406 that may identify, for example, the type of medication, dosage instructions for the medication, the number of refills available for the medication, the expiration date for the medication, and other information known to one skilled in the art. A display screen 408 is integrated into the sidewall of container body 400, which enables display of various types of information. The displayed information may comprise, for example, dispensation instructions for the medication within smart container 106 and other information relating to smart container 106 or the medication therein, as described below. In this embodiment, display screen 408 comprises an electronic digital display such as a dot-matrix display, although other types of displays may be used in accordance with the present invention.

Container body 400 also includes an open/close button 410 positioned on lip 402. Button 410 is moveable between an open position (in which button 410 is not depressed) and a closed position (in which button 410 is depressed). It can be appreciated that button 410 will be in the open position when cap 404 is not secured to container body 400 and, conversely, button 410 will be in the closed position when cap 404 is secured to container body 400. Button 410 is connected to a switch mechanism (not shown) that is configured to detect the open/close state of smart container 106. When the switch mechanism indicates that smart container 106 has been manipulated to its open state (e.g., when cap 404 is removed from container body 400), smart container 106 is configured to transmit a notification to central server 102 so as to update the transaction history of smart container 106, as described in greater detail below.

Figure 6:
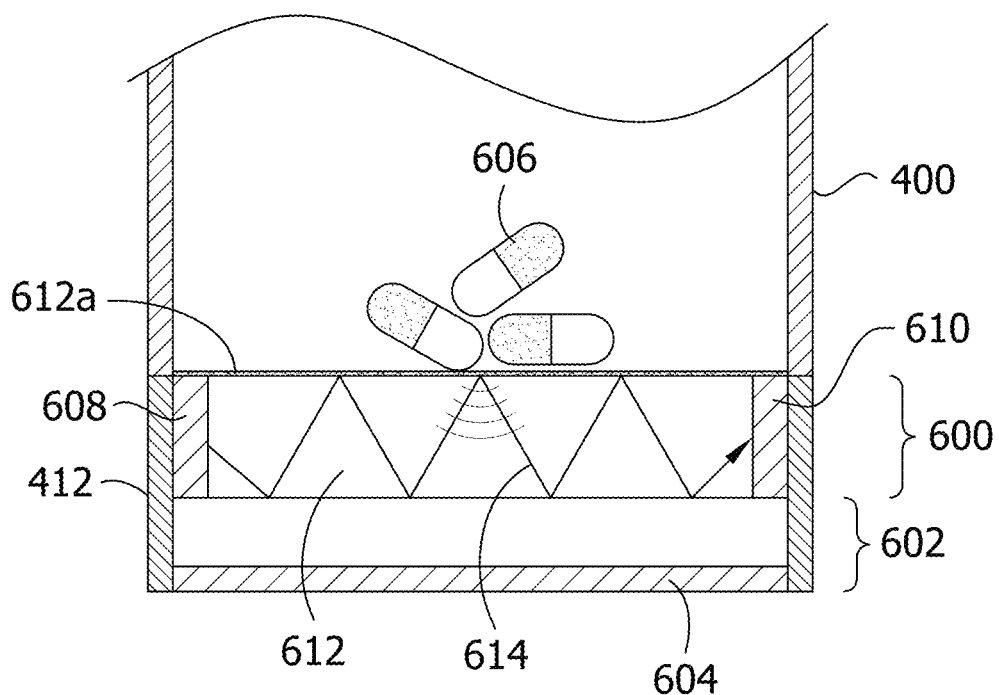
FIG. 6 is a schematic of a weight measurement system and electronic circuit board included in the base section of the smart container shown in FIG. 4.

Container body 400 further includes a base section 412 at its bottom end. As shown in FIG. 6, base section 412 includes a first compartment 600 configured to contain a weight measurement system (described below with reference to FIG. 6) and a second compartment 602 configured to contain an electronic circuit board 604 (described below with reference to FIG. 8). In this embodiment, base section 412 is fully enclosed so as to protect the components therein, and a suitable connection is provided on the bottom of base section 412 to enable charging of a rechargeable battery provided on electronic circuit board 604. In other embodiments, the battery is not rechargeable, in which case base section 412 includes a battery cover that may be opened to enable changing of the battery. Of course, one or both of the weight measurement system and electronic circuit board 604 could alternatively be integrated into a sidewall of container body 400.

FIG. 6 illustrates an exemplary embodiment of the weight measurement system contained within first compartment 600 of base section 412, which may be used in combination with a processor 800 of electronic circuit board 604 (shown in FIG. 8) to determine the weight of a medication 606 placed within the interior cavity of container body 400. The weight measurement system includes a light emitter 608 spaced apart from a light receiver 610 with a light transmission medium 612 positioned between them. In this embodiment, light emitter 608 comprises a light emitting diode (LED) and light receiver 610 comprises a photodiode, although other types of light emitters and light receivers may also be used in accordance with the present invention. The wavelength of the light may fall in the visible or non-visible portions of the electromagnetic spectrum. In this embodiment, the light comprises non-visible infrared light, i.e., light having a wavelength between 780 nm and 1 mm.

Light transmission medium 612 may be made of glass, plastic, or any material that enables the transmission of light from light emitter 608 to light receiver 610. A conductive layer 612a is provided on the top surface of light transmission medium 612 so as to form a capacitive sensor. In this embodiment, light transmission medium 612 comprises a glass screen and conductive layer 612a comprises a metallic lining on the top surface of the glass screen. As described below, when medication 606 is positioned within the interior cavity of container body 400, it causes a force to be applied to conductive layer 612a which decreases the amount of light received by light receiver 610. The amount of light received by light receiver 610 may then be used to determine the weight of medication 606.

Light emitter 608 is configured to emit light that travels through light transmission medium 612 to light receiver 610 in a light path indicated by line 614 in FIG. 6. As can be seen, the emitted light travels at an angle until it strikes the bottom surface of light transmission medium 612, at which point the light is substantially internally reflected at substantially the same angle. The light then continues to travel at substantially the same angle until it strikes the top surface of light transmission medium 612, at which point the light is again substantially internally reflected at substantially the same angle. This process repeats until the light reaches light receiver 610, at which point the light is substantially absorbed and the amount of energy is measured.

If a force is applied to conductive layer 612a due to the weight of medication 606, then less of the light will be internally reflected when it strikes the top surface of light transmission medium 612 (a concept known as "Frustrated Total Internal Reflection"). The level of attenuation of the light received by light receiver 610 will be dependent on the total weight of medication 606 positioned on conductive layer 612a—i.e., the amount of light transmitted through light transmission medium 612 to light receiver 610 will decrease as the weight of medication 606 increases.

Figure 8:
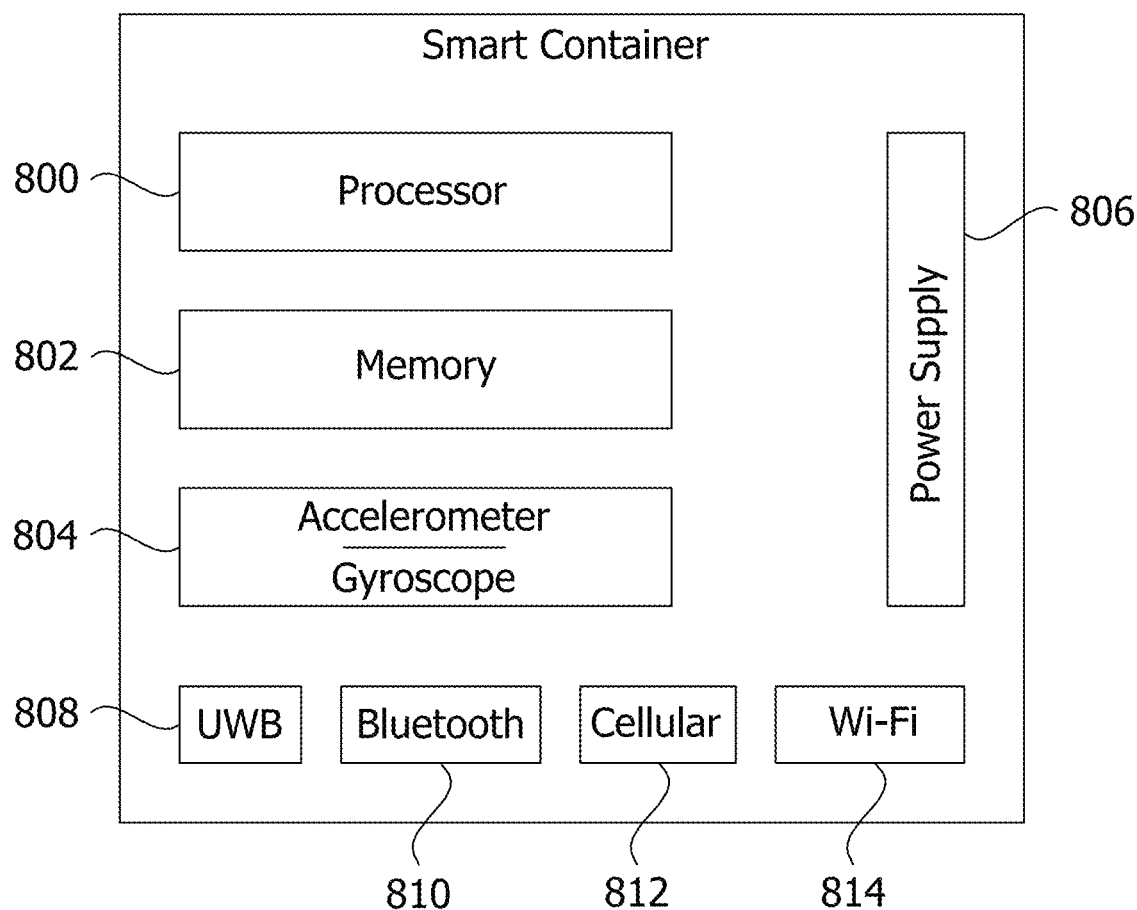
FIG. 8 is a block diagram of the electronic circuit of the smart container shown in FIG. 4.

Light emitter 608 and light receiver 610 are incorporated into a light intensity measurement circuit configured to provide a light intensity measurement to processor 800 provided on electronic circuit board 604 (shown in FIG. 8). Processor 800 is programmed to correlate the light intensity measurement to a weight of medication 606, which is calibrated from a "base" light intensity measurement with no medication positioned on conductive layer 612*a*. Thus, the weight measurement system shown in FIG. 6 functions as an "infrared scale" that can be used to determine whether contents have been added to or removed from smart container 400, as described in greater detail below.

Of course, it should be understood that other types of weight measurement systems may be used in accordance with the present invention. For example, in another exemplary embodiment, the weight measurement system contained within first compartment 600 of base section 412 comprises a digital scale. The digital scale includes one or more strain gauge load cells, e.g., four strain gauge elements electrically connected to form a Wheatstone bridge circuit. As known to one skilled in the art, the weight of medication 606 will cause a change in the resistance of the electrical conductors of the load cell—i.e. the resistance will decrease as the electrical conductors are compressed and the resistance will increase as the electrical conductors are stretched—which causes a change in the output voltage of the strain gauge circuit. Processor 800 is programmed to correlate an output voltage measurement to a weight of medication 606, which is calibrated from a "base" voltage measurement with no medication positioned within the interior cavity of container body 400. Similar to the infrared scale, the digital scale with strain gauge load cells can be used to determine whether contents have been added to or removed from smart container 400, as described in greater detail below.

Figure 7:
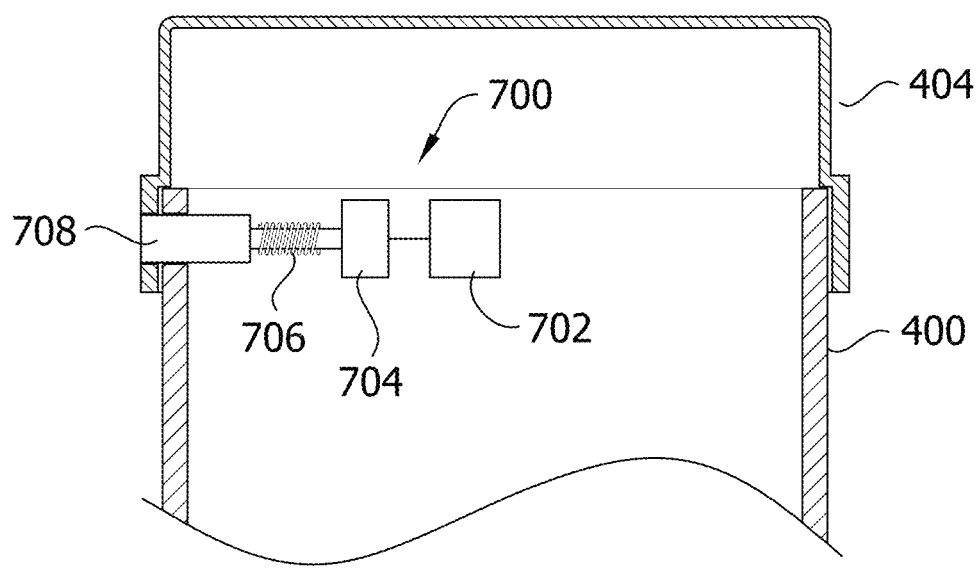
FIG. 7 is a schematic of a lock mechanism included in the upper lip of the smart container shown in FIG. 4.

Referring to FIG. 7, container body 402 further includes a lock mechanism 700 positioned on lip 402 of container body 400, which may be used in combination with processor 800 of electronic circuit board 604 (shown in FIG. 8) to prevent removal of cap 404 from container body 400. Lock mechanism 700 includes a direct current (DC) motor 702 that receives an actuation signal from processor 800. Upon actuation, DC motor 702 causes an actuator 704 to move a spring-loaded piston 706, which in turn pushes a latch 708 out from an opening in lip 402 and into contact with cap 404. It will be seen that central server 102 may transmit a lock signal to dynamically disable smart container 106, for example, if overdose thresholds are met or if it has been determined that the medication is having adverse effects on a patient's behavior. It can be appreciated that lock mechanism 700 will only function for its intended purpose if cap 404 is placed on container body 400. Of course, it should be understood that other types of lock mechanisms may be used in accordance with the present invention.

As noted above with reference to FIG. 6, second compartment 602 of base section 412 contains an electronic circuit board 604. FIG. 8 is a block diagram illustrating an exemplary embodiment of electronic circuit board 604, which includes an onboard processor 800 that is operatively connected to various hardware and software components, including a memory 802, an accelerometer and gyroscope 804, a power supply 806, and a wireless communications subsystem that includes a UWB transceiver 808, a Bluetooth transceiver 810, a cellular transceiver 812, and a Wi-Fi transceiver 814. Of course, processor 800 is also operatively connected to display 408 (shown in FIG. 4), open/close button 410 (shown in FIG. 4), light emitter 608 and light receiver 610 (shown in FIG. 6), and DC motor 702 (shown in FIG. 7), as described above.

Processor 800 may comprise a central processing unit (CPU), a multi-core processor, multiple processors, or some other type of processor, depending on the particular implementation. Processor 800 is operatively connected to memory 802, which may comprise any suitable combination of volatile memory (e.g., random-access memory (RAM)) and non-volatile memory (e.g. read-only memory (ROM), electrically erasable programmable read-only memory (EEPROM), or flash memory). Memory 802 stores firmware execution code instructions that, when executed by processor 800, cause processor 800 and the various hardware components of smart container 106 to perform the methods described herein, as described in greater detail below in connection with FIGS. 10A-10B. Memory also stores a unique container identifier and data obtained through execution of the firmware execution code (including, but not limited to, the last known valid configuration data—e.g., the medication within smart container 106, the weight of the medication, and the user identifier of the last known registered user having access to smart container 106).

Processor 300 is also operatively connected to accelerometer and gyroscope 806, which are configured to detect the orientation and rotation, respectively, of smart container 106. Also, power supply 806 is provided to supply power to the components of smart container 106. In this embodiment, power supply 806 comprises a rechargeable battery. Of course, other types of power sources may also be used in accordance with the present invention.

Processor 800 is also operatively connected to UWB transceiver 808 and Bluetooth transceiver 810 each of which enables short-range communication with one of user devices $104_1$-$104_n$. UWB transceiver 808 is configured to enable communication with one of user devices $104_1$-$104_n$ in accordance with the IEEE 802.15.4 protocol. Bluetooth transceiver 810 is configured to enable communication with one of user devices $104_1$-$104_n$ in accordance with the IEEE 802.15.1 protocol. Of course, other types of communication interfaces may also be used in accordance with the present invention (e.g., Wi-Fi Direct).

In some cases, smart container 106 detects access by a user carrying a user device that supports UWB (but not Bluetooth), in which case UWB transceiver 808 is used to communicate with the user device. In other cases, smart container 106 detects access by a user carrying a user device that supports Bluetooth (but not UWB), in which case Bluetooth transceiver 810 is used to communicate with the user device. In yet other cases, smart container 106 detects access by a user carrying a user device that includes both UWB and Bluetooth capabilities (e.g., user device 104 described above). In that case, UWB transceiver 808 is preferably used as the default for communication with the user device due to the superior performance capabilities of UWB compared to other short-range communication protocols, as discussed below. It can be appreciated that the inclusion of both UWB and Bluetooth capabilities in smart container 106 enables communication with many different types of user devices.

As just noted, UWB has superior performance capabilities compared to other short-range communication protocols, such as Bluetooth or Wi-Fi. For example, UWB supports a higher data exchange rate than other communication protocols, e.g., the data exchange rate between UWB-enabled devices is 27 megabits/second or greater. Also, UWB is more energy efficient than other communication protocols, e.g., UWB requires less than 1 milliwatt of power. In addition, UWB provides reduced radio frequency noise interference than other communication protocols. Moreover, UWB provides more precise location tracking than other communication protocols, e.g., a first UWB-enabled device can detect the location of a second UWB-enabled device at a distance of up to at least 10 meters and down to the centimeter level of location accuracy—this capability is used by smart container 106 to detect a user device, as described in greater detail below with reference to FIGS. 10A-10B.

Processor 800 is also operatively connected to cellular transceiver 812 and Wi-Fi transceiver 814 each of which enables long-range communication with central server 102. Cellular transceiver 812 is configured to enable communication with central server 102 in accordance with a cellular protocol, such as those that operate using the Long-Term Evolution (LTE) standard, the Universal Mobile Telecommunications System (UMTS) standard, and the like. Wi-Fi transceiver 814 is configured to enable communication with a local Wi-Fi network in accordance with the IEEE 802.11 protocol, wherein the local Wi-Fi network enables communication with central server 102. Of course, other types of communication interfaces may also be used in accordance with the present invention.

In this embodiment, smart container 106 has two methods of network communication with central server 102: (1) smart container 106 can transmit messages to central server 102 via cellular transceiver 812 or Wi-Fi transceiver 814 or (2) smart container 106 can transmit messages to a user device via UWB transceiver 808 or Bluetooth transceiver 810 (or even Wi-Fi transceiver 814), wherein the user device serves as a proxy to transmit the messages to central server 102. Of course, the latter method requires that the user device includes cellular and/or Wi-Fi capabilities, such as user device 104. In this case, user device 104 may receive messages from smart container 106 via UWB transceiver 310 or Bluetooth transceiver 312 (or even Wi-Fi transceiver 316), and then proxy the messages to central server 102 via cellular transceiver 314 or Wi-Fi transceiver 316. If smart container 106 loses connectivity with central server 102, a buffer of non-reported messages is locally stored in memory 802 until network communication is re-established with central server 102 or until a proxy communication is established with central server 102 via user device 104.

In some embodiments, the smart container is only configured to enable short-range communication with one of user devices $104_1$-$104_n$, e.g., the smart container includes a UWB transceiver and/or a Bluetooth transceiver (but not a cellular transceiver and/or a Wi-Fi transceiver). In this case, the smart container may transmit messages to a user device via the UWB transceiver and/or Bluetooth transceiver, wherein the user device serves as a proxy to transmit the messages to central server 102. Of course, these embodiments require that the user device includes cellular and/or Wi-Fi capabilities, such as user device 104.

Figure 5:
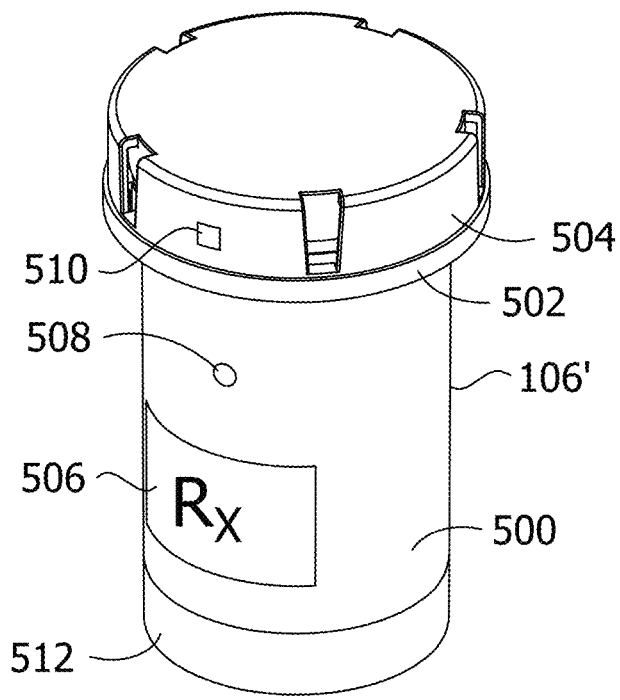
FIG. 5 is a front perspective view of an exemplary smart container that includes a light emitting diode (LED) for providing notifications, which may be used as one of the smart containers shown in FIG. 1.

FIG. 5 illustrates another exemplary embodiment of a smart container 106' that may be used as one of smart containers $106_1$-$106_n$. Smart container 106' has a configuration that is substantially the same as that of smart container 106 shown in FIGS. 4 and 6-8. Specifically, smart container 106' includes a container body 500 with a lip 502, a cap 504, a prescription label 506, an open/close button 510, a lock mechanism (not shown) positioned on lip 502, and a base section 512 that contains a weight measurement system (not shown) and an electronic circuit board (not shown). These components have the same configurations as the corresponding components of smart container 106 and will not be further described herein. The sole difference between smart container 106 and smart container 106' is that smart container 106' includes a light emitting diode (LED) 508 in place of display screen 408 of smart container 106. LED 508 is integrated into the sidewall of container body 502 and may be used to provide dispensation instructions for the medication within smart container 106', as described below.

Methods/Software Functionality

The description of the smart container platform provided above references various methods (i.e., software functionality) that are performed by central server 102, user devices $104_1$-$104_n$, and smart containers $106_1$-$106_n$. These methods will now be described with reference to FIG. 9 (registration process), FIGS. 10A-10B (management of user session), FIGS. 11A-11B (creation of transaction history), and FIG. 12 (provision of notifications).

Registration Process

As noted above, central server 102 enables all individuals who have a need to access one or more of smart containers $106_1$-$106_n$ to register with the smart container platform. In general, the registration process enables each individual to obtain a user identifier and a role designation within the smart container platform that is stored on the user device (i.e., one of user devices $104_1$-$104_n$) carried by the individual.

Figure 9:
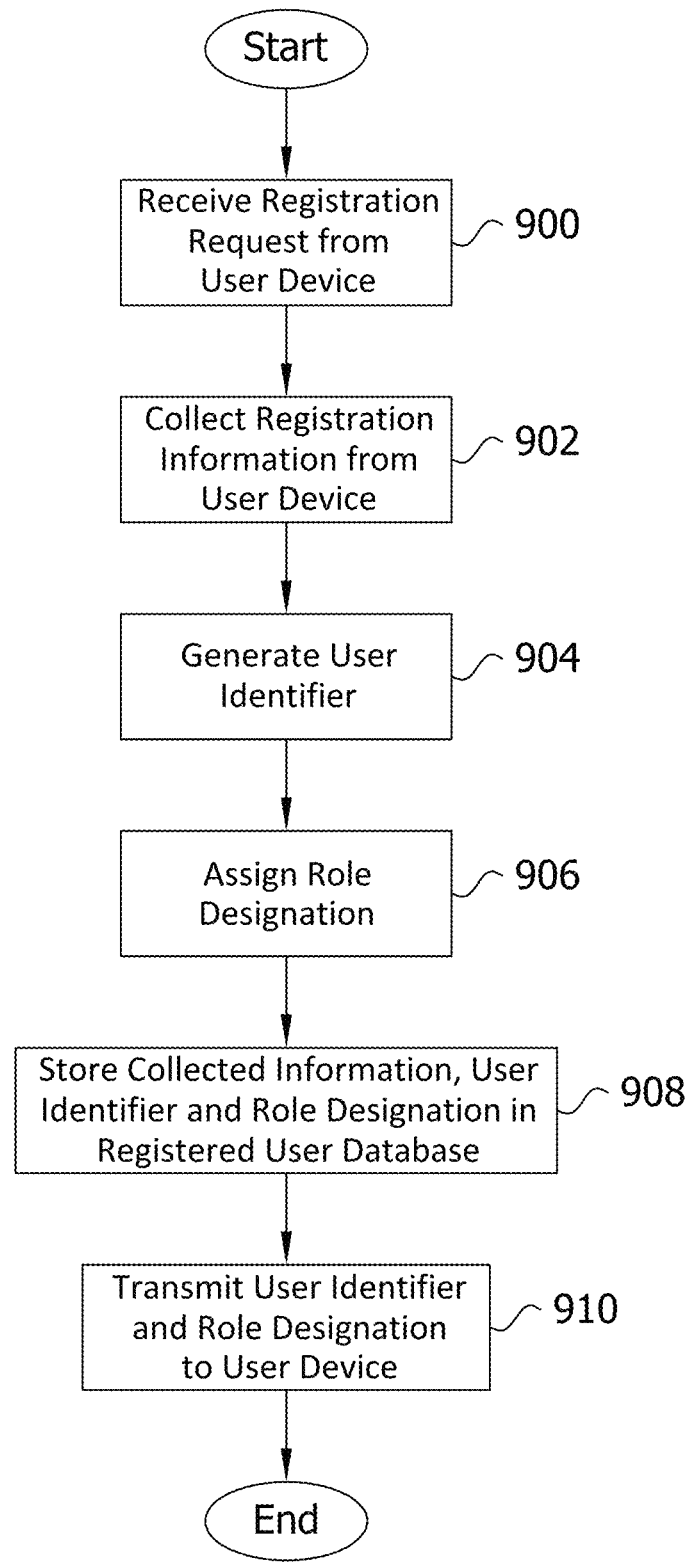
FIG. 9 is a process flow diagram of an exemplary method of registering users from the perspective of the central server shown in FIG. 1.

Referring to FIG. 9, a method of registering users within the smart container platform in accordance with one embodiment of the present invention is described with reference to steps 900-910. It should be understood that this method is described from the perspective of central server 102.

In step 900, central server 102 receives a registration request from one of user devices $104_1$-$104_n$, such as user device 104. In one embodiment, the user opens smart container application 318 on user device 104 and sends a registration request to central server 102. Upon receipt of the registration request, central server 102 executes the registration module of monitoring application 204 and provides a user interface that enables smart container application 318 to display various web pages on display 304 of user device 104. Central server 102 may communicate with user device 104 via Hypertext Transfer Protocol (HTTP) (e.g., HTTP/1.0, HTTP/1.1 plus, HTTP/2, or HTTP/3), Hypertext Transfer Protocol Secure (HTTPS), or any other network protocol used to distribute web pages. The web pages prompt the user to input registration information via display 304 of user device 104. The registration information may include, for example, information about the user's identity (e.g., name, address, etc.) and, as applicable, information about the user's employer (e.g., company name, address, etc.) and the user's position with the employer (e.g., pharmacist, logistics personnel, etc.). In some embodiments, some or all of the registration information can be collected from another computing device or automatically obtained from an existing user profile associated with the user that is maintained by central server 102.

In step 902, central server 102 collects the registration information provided by the user to create a user profile. In step 904, central server 102 generates a user identifier for the user, e.g., a GUID or any other type of unique credentials. In step 906, central server 102 assigns a role designation to the user based on the collected registration information. For example, if the registration information indicates that the individual is a pharmacist who is employed by a pharmaceutical fulfillment system, then the individual will be assigned a "manipulator" role designation or equivalent. Other role designations may include, for example, "transporter," "receiver," or "consumer," or their equivalents. As further described herein, the registration process can define a hierarchy of users and designated roles that determine the rules governing each user's access to one or more of smart containers $106_1$-$106_n$.

In step 908, central server 102 stores the user profile in association with the user identifier and role designation in registered user database 206. It can be appreciated that this information can be used to identify the user in subsequent communications with central server 102. Then, in step 910, central server 102 returns a registration acknowledgement along with the user identifier and role designation to user device 104.

Of course, it should be understood that steps 900-908 are performed for each individual who desires to register with the smart container platform.

Management of User Session

As noted above, each of smart containers $106_1$-$106_n$ is configured to manage a user session with one or more of user devices $104_1$-$104_n$, i.e., the user devices carried by the users within the acknowledged set for the smart container. The acknowledged set may include, for example, a pharmacist, logistics company personnel, a family member or caretaker, and a patient. Of course, other individuals may be included in the acknowledged set for a particular smart container.

Figure 10A:
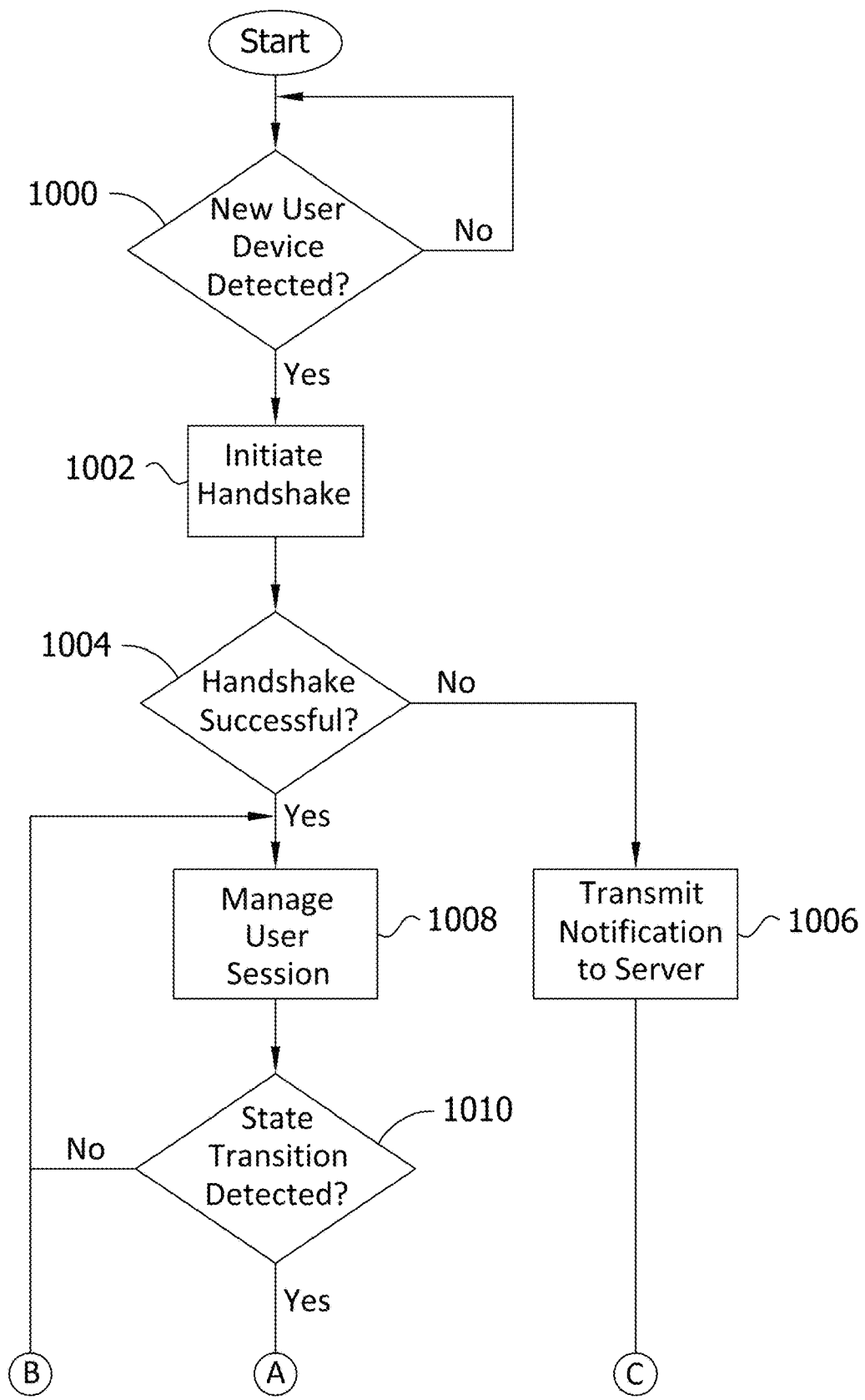
FIGS. 10A-10B are process flow diagrams of an exemplary method of managing a user session with a user device from the perspective of one of the smart containers shown in FIG. 1.
Figure 10B:
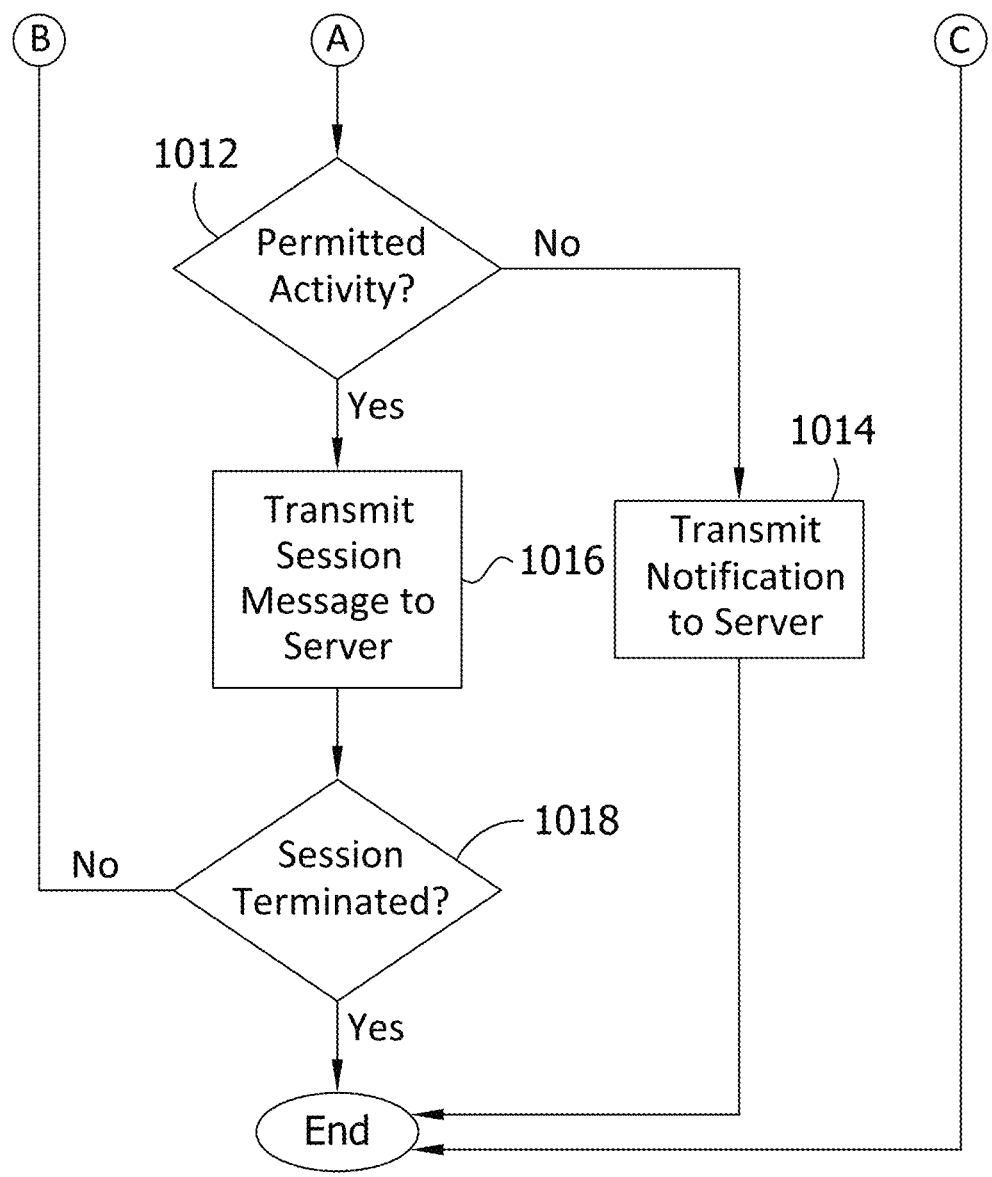

Referring to FIGS. 10A-10B, an exemplary method of managing a user session with one of user devices $104_1$-$104_n$ is described below with reference to steps 1000-1018. It should be understood that this method is described from the perspective of one of smart containers $106_1$-$106_n$, such as smart container 106.

In step 1000, smart container 106 determines if a new user device has been detected, i.e., a user device carried by a user in possession of smart container 106. In some embodiments, it is assumed that a user has possession of smart container 106 when the user device is in substantially constant proximity to smart container 106 for a predetermined period of time, for example, when the user device is located a distance of about 30 inches or less from smart container 106 for a time period of about 30 seconds or more. Of course, the distance and time period are configurable and may vary between implementations. Preferably, smart container 106 uses UWB pulses to determine the proximity of the user device, which provides more precise location tracking than other communication protocols.

In other embodiments, it is assumed that a user has possession of smart container 106 when the proximity requirement is met, as described above, and additionally when movement of the user device is detected. Movement of the user device may be detected, for example, using an application on the user device. This additional requirement may be used to detect a user device carried by a registered user who is transporting smart container 106, while avoiding detection of a user device carried by a user sitting close to, but not in possession of, smart container 106.

In yet other embodiments, it is assumed that a user has possession of smart container 106 when the proximity requirement is met, as described above, and additionally when movement and/or a change in orientation of smart container 106 is detected. Movement and/or a change in orientation of smart container 106 may be detected, for example, using the accelerometer and gyroscope provided on smart container 106. This additional requirement may be used to detect a user device carried by a user who is holding or picking up smart container 106.

Of course, one skilled in the art will appreciate that other requirements may also be implemented to detect the desired user devices in accordance with the present invention.

If a new user device is not detected, then the process returns to step 1000. However, if a new user device is detected, then smart container 106 initiates a handshake protocol with the user device in step 1002. In step 1004, it is determined whether the handshake is successful. If the handshake is not successful, then the process proceeds to step 1006. However, if the handshake is successful, then the process proceeds to step 1008.

In some embodiments, smart container 106 stores configuration data (including the container identifier) in a well-defined object format and initiates the handshake protocol by transmitting the configuration data to the user device via UWB transceiver 808 or Bluetooth transceiver 810. If the user device has smart container application 318 installed thereon and has obtained a user identifier through the registration process, then smart container application 318 uses the configuration data to form a session object (including the container identifier and user identifier) and communicates that session object to central server 102. Central server 102 stores the session object and will correlate all session messages to the session object, as described below with reference to FIGS. 11A-11B. Central server 102 then sends a confirmation message back to smart container 106. Thus, in this instance, the handshake is successful.

On the other hand, if the user device does not have smart container application 318 installed thereon (e.g., if the user device is carried by a non-registered user), then the user device will not be able to interpret the configuration data transmitted by smart container 106 and will not be able to transmit a session object to central server 102. As such, smart container 106 will not receive a confirmation message from central server 102. Thus, in this instance, the handshake is not successful.

In step 1006, if the handshake is not successful (i.e., if the confirmation message is not received after a threshold timeout), then smart container 106 logs the unsuccessful attempt to communicate with the user device and transmits a notification to central server 102 via cellular transceiver 812 or Wi-Fi transceiver 814. Central server 102 then makes a network call to smart container 106 to obtain the user identifier of the last known registered user having access to smart container 106 (i.e., the user identifier associated with the last successful handshake). Central server 102 then stores this information in the transaction history of smart container 106 for audit purposes-either in smart container database 208 or on a distributed ledger via API server 108. Central server 102 may also provide this information to one or more users within the acknowledged set (e.g., the pharmacist, medical professional and/or patient) for further assessment and possible locking of smart container 106 and/or return of smart container 106 to the sender (although the information may be disregarded if deemed innocuous).

In step 1008, if the handshake is successful, then smart container 106 manages a user session with the user device. In some embodiments, smart container 106 provides various types of notifications or feedback on the container itself during the user session, particularly if the user is a patient. These notifications or feedback may be provided via display 408 (shown in FIG. 4) or LED 508 (shown in FIG. 6).

In some embodiments, smart container 106 utilizes display 408 and/or LED 508 to provide a notification to the user of the dispensing time for medication 606—i.e., the time remaining until medication 606 should be dispensed and/or the time that has passed since medication 606 should have been dispensed. In one embodiment, the notification is presented in textual form on display 408. In another embodiment, the color of LED 508 is changed to reflect the notification, e.g., LED 508 may change from yellow to green as the dispensing time approaches and then change to a flashing red after the dispensing time has passed.

In some embodiments, smart container 106 utilizes display 408 and/or LED 508 to provide dosing instructions to the user while medication 606 is being dispensed. In one embodiment, as the user extracts medication 606 from smart container 106, a notification is presented in textual form on display 408 of "continue dispensing pills" or "too many pills dispensed." A counter may also be displayed once medication 606 has been dispensed, such as "1 more pill remaining." In another embodiment, LED 508 is illuminated as the user extracts medication 606 from smart container 106, and then LED 508 is turned off once correct dispensing has occurred.

It can be appreciated that smart container 106 is able to determine how much medication 606 has been dispensed using the weight measurement system positioned in base section 412, as described above. For example, processor 800 may be programmed to calculate the amount of medication 606 dispensed based on (1) the weight change of medication 606 during the dispensing period and (2) the known weight of a single pill. This same method may also be used for other types of medications, such as medications in liquid form.

In order to provide the notifications and feedback described above, smart container 106 maintains medication and dosage information in memory 802. This information may include, for example, the total number of pills in the prescription, the prescribed dosage of medication, the number of pills dispensed and/or remaining, weight information, and the like. It should be understood that some of this information may be downloaded from central server 102 to smart container 106 (e.g., a pharmacist may initially upload certain information to central server 102 when initializing smart container 106), while other information is tracked by smart container 106 during the user session with the patient.

In some embodiments, smart container 106 is part of a group of smart containers provided to a patient, i.e., a pharmacist establishes a group of in smart containers that share a common group identifier. The pharmacist may enable group rules such as the maximum number of pills in the group that may be dispensed at a given time, usage abuse warnings, adherence warnings, automated drug interaction lockouts, and mandatory ordering of smart containers in the group. Preferably, central server 102 manages the group via communication with each of the smart containers in the group.

In some embodiments, each smart container in the group transmits a notification to central server 102 as medication is dispensed. Central server 102 evaluates the notifications and provides an alert of any violation of the group rules. The alert may be transmitted to one or more smart containers in the group so that the alert may be communicated via their respective displays (e.g., display 408) and/or LEDs (e.g., LED 508). The alert may also be transmitted to the user device carried by one or more users within the acknowledged set (e.g., the pharmacist, medical professional, family member, caretaker and/or patient). Central server 102 may also transmit a disable signal to dynamically lock one or more smart containers in the group as required.

In some embodiments, the smart containers in the group utilize their respective displays (e.g., display 408) and/or LEDs (e.g., LED 508) to provide guidance on which medications to administer and/or the order in which to administer the medications. In one embodiment, the guidance is presented in textual form on display 408. In another embodiment, the LEDs of a particular combination of smart containers are illuminated to signify that those medications should be administered together, and the LEDs are turned off when correct dispensing has occurred. In yet another embodiment, the LED of the smart container for the next medication to be administered blinks green, while the LEDs of the smart containers for medications that have already been dispensed are red. Other guidance schemes will be apparent to one skilled in the art.

In step 1010, smart container 106 determines whether a state transition has occurred during the user session. State transitions include, for example, movement of smart container 106, opening of smart container 106, extraction of contents from smart container 106, or addition of contents to smart container 106. Of course, other types of events/state transitions may be detected in accordance with the present invention. If no state transition is detected, the process returns to step 1008. However, if a state transition is detected, in step 1012, smart container 106 determines whether the state transition is a permitted activity for the registered user based on the user's role designation. For example, a registered user having a "consumer" role designation would be allowed to open the smart container, but a registered user having a "transporter" role designation would typically not have opening rights.

In step 1014, if the state transition is not a permitted activity for the registered user, smart container 106 transmits a notification to central server 102 via cellular transceiver 812 or Wi-Fi transceiver 814 (or to the user device via UWB transceiver 808 or Bluetooth transceiver 810, which proxies the session message to central server 102). Central server 102 then stores this information in the transaction history of smart container 106 for audit purposes-either in smart container database 208 or on a distributed ledger via API server 108. Central server 102 may also provide this information to one or more users within the acknowledged set (e.g., the pharmacist, medical professional and/or patient) for further assessment and possible locking of smart container 106 and/or return of smart container 106 to the sender (although the information may be disregarded if deemed innocuous).

In step 1016, if the state transition is a permitted activity for the registered user, smart container 106 transmits a session message to central server 102 via cellular transceiver 812 or Wi-Fi transceiver 814 (or to the user device via UWB transceiver 808 or Bluetooth transceiver 810, which proxies the session message to central server 102). Central server 102 then stores this information in the transaction history of smart container 106 for audit purposes-either in smart container database 208 or on a distributed ledger via API server 108.

In step 1018, smart container 106 determines whether the user session has terminated. In some embodiments, the user session is terminated when a new user is detected (e.g., when one user within the acknowledged set hands off smart container 106 to another user within the acknowledged set). In other embodiments, the user session is terminated when the user is no longer in proximity to smart container 106. If the user session is not terminated, then the process returns to step 1008. However, if the user session is terminated, then the process ends.

Of course, it should be understood that steps 1000-1018 are performed for each of the users within the acknowledged set.

Creation of Transaction History

As noted above, a number of different users will have access to each of smart containers $106_1$-$106_n$ during the life cycle of the smart container. During each user session, central server 102 receives messages relating to various types of access to the smart container by the individuals within the acknowledged set. For example, all transfers of the smart container between individuals within the acknowledged set are logged with the central server. Other events may also be logged with the central server, such as movement of the smart container, opening of the smart container, extraction of contents from the smart container, or addition of contents to the smart container. This enables the creation of a full transaction history of the smart container and ensures that access is only allowed to those individuals within the acknowledged set.

Figure 11A:
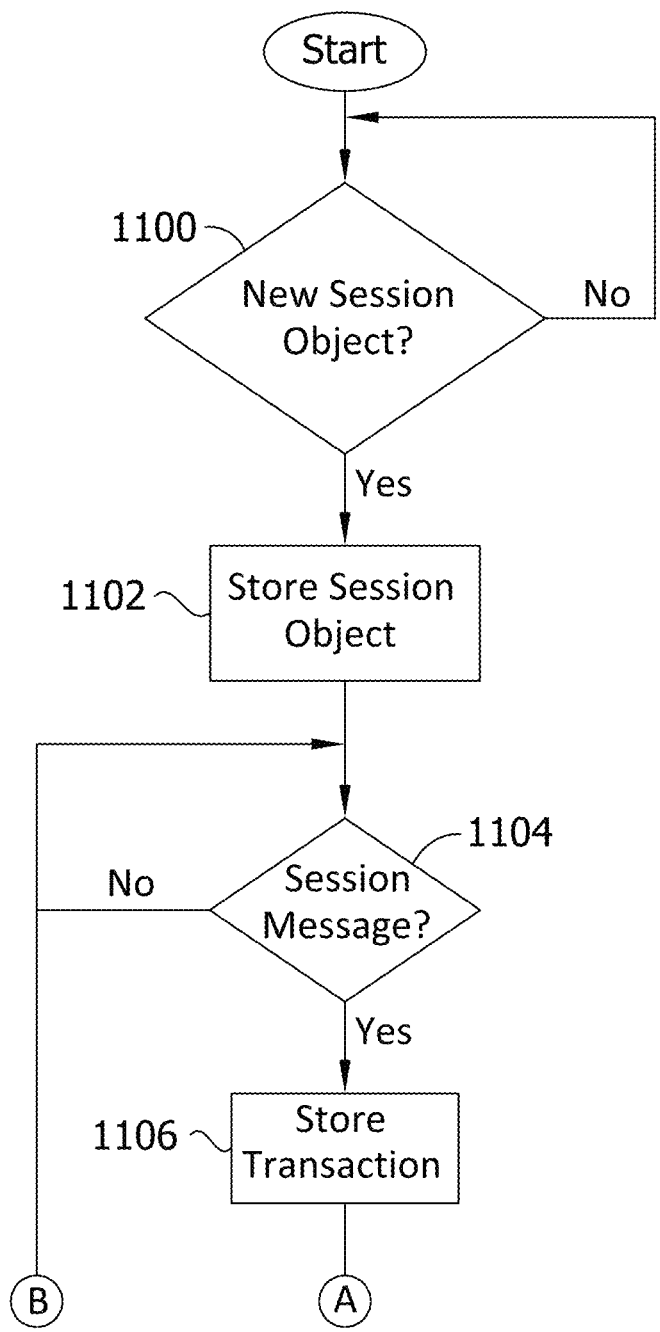
FIGS. 11A-11B is a process flow diagram of an exemplary method of creating a transaction history for a smart container from the perspective of the central server shown in FIG. 1.
Figure 11B:
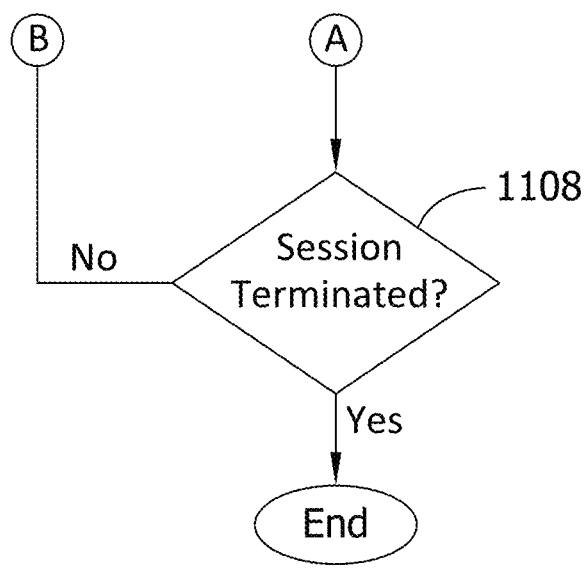

Referring to FIGS. 11A-11B, an exemplary method of creating a transaction history for one of smart containers $106_1$-$106_n$, such as smart container 106, is described below with reference to steps 1100-1108. It should be understood that this method is described from the perspective of central server 102.

In step 1100, central server 102 determines whether it has received a new session object from a user device, i.e., a user device carried by a user within the acknowledged set. As described above, a new session object will be received when there is a successful handshake between the user device and smart container 106. If a new session object has not been received, then the process returns to step 1100. However, if a new session object is received, then central server 102 stores the session object in step 1102.

In step 1104, central server 102 determines whether a session message has been received during the user session. A session message is received, for example, when a state transition is detected during the user session (e.g., movement of smart container 106, opening of smart container 106, extraction of contents from smart container 106, or addition of contents to smart container 106) or a notification is transmitted by smart container 106. If a new session message has not been received, then the process returns to step 1104. However, in step 1106, if a new session message is received, then a transaction corresponding to the session message is stored in the transaction history of smart container 106 for audit purposes-either in smart container database 208 or on a distributed ledger via API server 108. In step 1108, central server 102 determines whether the user session has terminated. If the user session has not been terminated, then the process returns to step 1104. However, if the user session is terminated, then the process ends.

Of course, it should be understood that steps 1100-1108 are performed for each of the users within the acknowledged set.

Provision of Notifications

During the life cycle of a smart container, central server 102 may transmit various notifications to the user device carried by one or more users within the acknowledged set (e.g., the pharmacist, medical professional, family member, caretaker and/or patient). The notifications may also be transmitted to the smart container itself so that the appropriate information may be communicated via an onboard display and/or an LED of the smart container. The information collected by central server 102 may also be integrated with a patient's electronic health record (EHR)/personal health record (PHR) and analyzed by the patient's medical support team, which enables a medical professional to analyze the data in near real time and trigger the transmission of a notification or warning.

In some embodiments, the notifications comprise push notifications from external sources, such as information on product availability and refills, new filling centers at which the prescription may be filled, or product recalls. In other embodiments, the notifications comprise adherence information, over-usage warnings, or misdiagnosis alerts. For example, upon notification of a product recall or misdiagnosis, the notification may be communicated in textual form to the user device of the patient or other users (e.g., a family member or caretaker). In addition, the notification may be displayed in textual form on the display of the smart container, or an LED may be illuminated to flash red so as to provide a warning to the patient. In extreme cases, such as when overdose thresholds are met or if the medication is determined to have an adverse effect on the patient's behavior, central server 102 may transmit a disable signal to dynamically lock the smart container.

Figure 12:
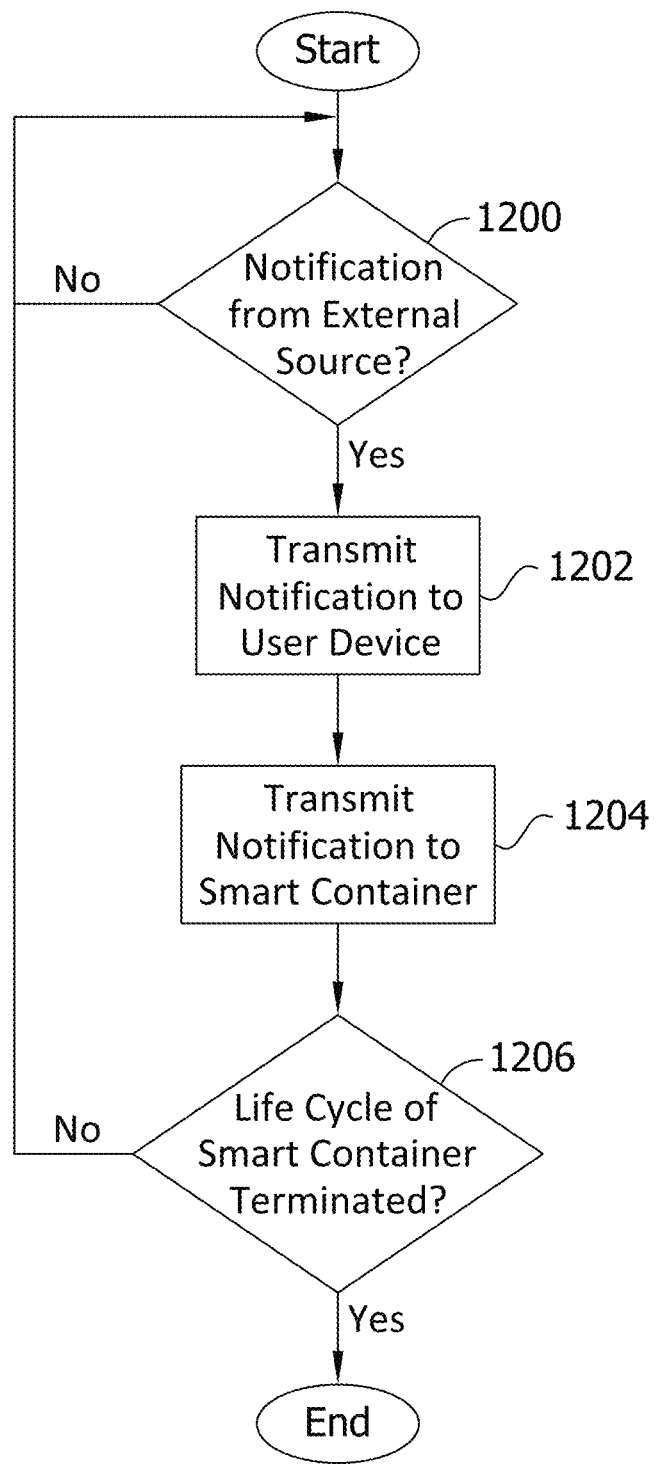
FIG. 12 is a process flow diagram of an exemplary method of providing notifications to a user device and/or a smart container from the perspective of the central server shown in FIG. 1.

Referring to FIG. 12, an exemplary method of providing notifications is described below with reference to steps 1200-1206. It should be understood that this method is described from the perspective of central server 102.

In step 1200, central server 102 determines whether a notification has been received from an external source. If not, then the process returns to step 1200. If a notification has been received, in step 1202, central server 102 transmits the notification to one or more user devices, i.e., the user device of one or more individuals within the acknowledged set. In step 1204, central server 102 also transmits the notification to the smart container itself so that the appropriate information may be communicated via an onboard display of the smart container (e.g., display 408) and/or an LED of the smart container (e.g., LED 508). In step 1206, central server 102 determines whether it is the end of the life cycle of the smart container. If not, then the process returns to step 1200. However, if the life cycle has ended, then the process ends.

General Information

The description set forth above provides several exemplary embodiments of the inventive subject matter. Although each exemplary embodiment represents a single combination of inventive elements, the inventive subject matter is considered to include all possible combinations of the disclosed elements. Thus, if one embodiment comprises elements A, B, and C, and a second embodiment comprises elements B and D, then the inventive subject matter is also considered to include other remaining combinations of A, B, C, or D, even if not explicitly disclosed.

The use of any and all examples or exemplary language (e.g., "such as" or "for example") provided with respect to certain embodiments is intended merely to better describe the invention and does not pose a limitation on the scope of the invention. No language in the description should be construed as indicating any non-claimed element essential to the practice of the invention.

The use of the terms "comprises," "comprising," or any other variation thereof, are intended to cover a non-exclusive inclusion, such that a system or method that comprises a list of elements does not include only those elements, but may include other elements not expressly listed or inherent to such system or method.

The recitation of ranges of values herein is merely intended to serve as a shorthand method of referring individually to each separate value falling within the range. Unless otherwise indicated, each individual value is incorporated into the description as if it were individually recited herein.

The use of relative relational terms, such as first and second, are used solely to distinguish one structure or action from another structure or action without necessarily requiring or implying any actual such relationship or order between such structures or actions.

Finally, while the present invention has been described and illustrated hereinabove with reference to various exemplary embodiments, it should be understood that various modifications could be made to these embodiments without departing from the scope of the invention. Therefore, the present invention is not to be limited to the specific systems or methods of the exemplary embodiments, except insofar as such limitations are included in the following claims.

What is claimed and desired to be secured by Letters Patent is as follows:

1. A storage system comprising:
    a container body having an interior space and that stores an item;
    a light transmission medium within the container body, wherein the light transmission medium divides the interior space into a first portion and a second portion, further wherein the item is disposed within the second portion;
    a light emitter fixed on a sidewall of the first portion and that emits emitted light into the first portion towards the light transmission medium, wherein the light transmission medium reflects the emitted light;
    a light receiver fixed on the sidewall of the first portion and opposed to the light emitter to receive the emitted light that is reflected by the light transmission medium and determine a light intensity measurement; and
    a processor that is configured to determine a weight of the item based on the light intensity measurement.

2. The storage system of claim 1, wherein the light emitter is a light emitting diode, and the light receiver is a photodiode.

3. The storage system of claim 1, wherein the emitted light has a wavelength that is in a non-visible portion of an electromagnetic spectrum.

4. The storage system of claim 1, wherein the light transmission medium includes:
    a conductive layer that forms a capacitive sensor based on the weight of the item; and
    a glass screen that supports the conductive layer.

5. The storage system of claim 4, wherein the conductive layer is a metallic lining disposed on top of the glass screen, and the emitted light travels through the glass screen.

6. The storage system of claim 1, wherein the light transmission medium includes:
    a first light transmission medium that supports the item and reflects the emitted light; and
    a second light transmission medium arranged opposite to the first light transmission medium and that reflects the emitted light reflected by the first light transmission medium.

7. The storage system of claim 1, wherein to determine the weight of the item, the processor is configured to:
    determine a level of attenuation of the emitted light based on the light intensity measurement; and
    determine the weight of the item based on the level of attenuation.

8. The storage system of claim 1, wherein the processor is configured to:
    execute a calibration based on a base light intensity measurement that is measured when no item is on the light transmission medium;
    wherein to determine the weight of the item, the processor is programmed to correlate the light intensity measurement to the weight of the item based on the calibration.

9. At least one non-transitory computer readable storage medium comprising a set of instructions, which when executed by a smart container, causes the smart container to:
    emit, with a light emitter, emitted light into a first portion of an interior space of a container body and towards a light transmission medium, wherein the light transmission medium reflects the emitted light, wherein the light transmission medium divides the interior space into the first portion and a second portion, further wherein an item is disposed within the second portion, wherein the light emitter is fixed on a sidewall of the first portion; and
    receive, with a light receiver, the emitted light that is reflected by the light transmission medium wherein the light receiver is fixed on the sidewall of the first portion and opposed to the light emitter;
    determine a light intensity measurement based on the emitted light received by the light receiver; and
    determine a weight of the item based on the light intensity measurement.

10. The at least one non-transitory computer readable storage medium of claim 9, wherein the light emitter is a light emitting diode, and the light receiver is a photodiode.

11. The at least one non-transitory computer readable storage medium of claim 9, wherein the emitted light has a wavelength that is in a non-visible portion of an electromagnetic spectrum.

12. The at least one non-transitory computer readable storage medium of claim 9, wherein the light transmission medium includes:
    a conductive layer that forms a capacitive sensor based on the weight of the item; and
    a glass screen that supports the conductive layer.

13. The at least one non-transitory computer readable storage medium of claim 12, wherein the conductive layer is a metallic lining disposed on top of the glass screen, and the emitted light travels through the glass screen.

14. The at least one non-transitory computer readable storage medium of claim 9, wherein the light transmission medium includes:
    a first light transmission medium that supports the item and reflects the emitted light; and
    a second light transmission medium arranged opposite to the first light transmission medium and that reflects the emitted light reflected by the first light transmission medium.

15. The at least one non-transitory computer readable storage medium of claim 9, wherein to determine the weight of the item, the instructions, when executed, cause the smart container to:

determine a level of attenuation of the emitted light based on the light intensity measurement; and determine the weight of the item based on the level of attenuation.

16. The at least one non-transitory computer readable storage medium of claim 9, wherein the instructions, when executed, causes the smart container to:

execute a calibration based on a base light intensity measurement that is measured when no item is on the light transmission medium;

wherein to determine the weight of the item, the instructions, when executed, causes the smart container to correlate the light intensity measurement to the weight of the item based on the calibration.

17. A method comprising:

emitting, with a light emitter, emitted light into a first portion of an interior space of a container body and towards a light transmission medium, wherein the light transmission medium reflects the emitted light, wherein the light transmission medium divides the interior space into the first portion and a second portion, further wherein an item is disposed within the second portion, wherein the light emitter is fixed on a sidewall of the first portion; and receiving, with a light receiver, the emitted light that is reflected by the light transmission medium wherein the light receiver is fixed on the sidewall of the first portion and opposed to the light emitter;

determining a light intensity measurement based on the emitted light received by the light receiver; and determining a weight of the item based on the light intensity measurement.

18. The method of claim 17, wherein the light emitter is a light emitting diode, and the light receiver is a photodiode.

19. The method of claim 17, wherein the emitted light has a wavelength that is in a non-visible portion of an electromagnetic spectrum.

20. The method of claim 17, wherein the light transmission medium includes:

a conductive layer that forms a capacitive sensor based on the weight of the item; and a glass screen that supports the conductive layer.

21. The method of claim 20, wherein the conductive layer is a metallic lining disposed on top of the glass screen, and the emitted light travels through the glass screen.

22. The method of claim 17, wherein the light transmission medium includes:

a first light transmission medium that supports the item and reflects the emitted light; and a second light transmission medium arranged opposite to the first light transmission medium and that reflects the emitted light reflected by the first light transmission medium.

23. The method of claim 17, further comprising:

executing a calibration based on a base light intensity measurement that is measured when no item is on the light transmission medium, wherein the determining the weight of the item comprises:

determining a level of attenuation of the emitted light based on the light intensity measurement;

determining the weight of the item based on the level of attenuation; and correlating the light intensity measurement to the weight of the item based on the calibration.

\* \* \* \* \*